United States Patent
Hacohen et al.

(10) Patent No.: US 10,045,845 B2
(45) Date of Patent: *Aug. 14, 2018

(54) PERCUTANEOUSLY-DELIVERABLE MECHANICAL VALVE

(71) Applicant: MITRALTECH LTD., Or Yehuda (IL)

(72) Inventors: Gil Hacohen, Ramat Gan (IL); Yuval Zipory, Modi'in (IL); Tal Reich, Moshav Moledet (IL); Eran Miller, Moshav Beit Elazari (IL); Amir Gross, Moshav Mazor (IL)

(73) Assignee: MITRALTECH LTD., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/354,504

(22) Filed: Nov. 17, 2016

(65) Prior Publication Data

US 2017/0065407 A1    Mar. 9, 2017

Related U.S. Application Data

(63) Continuation of application No. 14/442,541, filed as application No. PCT/IL2013/050937 on Nov. 13, (Continued)

(51) Int. Cl.
*A61F 2/24* (2006.01)

(52) U.S. Cl.
CPC .......... *A61F 2/2403* (2013.01); *A61F 2/2409* (2013.01); *A61F 2/2418* (2013.01); (Continued)

(58) Field of Classification Search
CPC .... A61F 2/2403; A61F 2/2469; A61F 2/2418; A61F 2/2415; A61F 2/24
See application file for complete search history.

(56) References Cited

U.S. PATENT DOCUMENTS

| 4,275,469 A | 6/1981 | Gabbay |
| 4,423,525 A | 1/1984 | Vallana et al. |

(Continued)

FOREIGN PATENT DOCUMENTS

| EP | 0170262 A2 | 2/1986 |
| WO | 2006/070372 A2 | 7/2006 |

(Continued)

OTHER PUBLICATIONS

Invitation to pay Additional Fees dated Sep. 29, 2017; PCT/IL2017/050873.

(Continued)

*Primary Examiner* — Jason-Dennis Stewart
(74) *Attorney, Agent, or Firm* — Ladas & Parry LLP

(57) ABSTRACT

Apparatus for regulating blood flow of a subject is provided, the apparatus comprising a prosthetic valve (20) that comprises a tubular element (22), shaped to define a lumen (23) therethrough, and a valve member (24), configured to be coupled to the tubular element (22) and to be disposed within the lumen (23). The prosthetic valve (20) has (1) a compressed configuration in which the lumen (23) has a compressed width, the valve member (24) is generally cylindrical, and the prosthetic valve (20) is configured to be percutaneously delivered into the subject, and (2) an expanded configuration in which the lumen (23) has an expanded width that is greater than the compressed width, and the valve member (24) is generally disc-shaped, is coupled to the tubular element (22), and is disposed within the lumen (23). Other embodiments are also described.

13 Claims, 6 Drawing Sheets

Related U.S. Application Data 2013, now Pat. No. 9,498,332, which is a continuation of application No. 13/675,119, filed on Nov. 13, 2012, now Pat. No. 8,628,571.

(52) U.S. Cl.
CPC .......... *A61F 2/2469* (2013.01); *A61F 2/2436* (2013.01); *A61F 2220/0008* (2013.01); *A61F 2220/0041* (2013.01); *A61F 2230/005* (2013.01); *A61F 2230/0013* (2013.01)

(56) References Cited

U.S. PATENT DOCUMENTS

| | | |
|---|---|---|
| 4,853,986 A | 8/1989 | Allen |
| 4,994,077 A | 2/1991 | Dobben |
| 5,078,739 A | 1/1992 | Martin |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,647,857 A | 7/1997 | Anderson et al. |
| 5,765,682 A | 6/1998 | Bley et al. |
| 5,873,906 A | 2/1999 | Lau et al. |
| 5,980,565 A | 11/1999 | Jayaraman |
| 6,016,882 A | 1/2000 | Ishikawa |
| 6,019,787 A | 2/2000 | Richard et al. |
| 6,059,827 A | 5/2000 | Fenton, Jr. |
| 6,165,210 A | 12/2000 | Lau et al. |
| 6,193,745 B1 | 2/2001 | Fogarty et al. |
| 6,287,339 B1 | 9/2001 | Vazquez et al. |
| 6,312,465 B1 | 11/2001 | Griffin et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,402,780 B2 | 6/2002 | Williamson, IV et al. |
| 6,454,799 B1 | 9/2002 | Schreck |
| 6,458,153 B1 | 10/2002 | Bailey et al. |
| 6,482,228 B1 | 11/2002 | Norred |
| 6,551,350 B1 | 4/2003 | Thornton et al. |
| 6,558,396 B1 | 5/2003 | Inoue |
| 6,719,788 B2 | 4/2004 | Cox |
| 6,733,525 B2 | 5/2004 | Yang et al. |
| 7,018,406 B2 | 3/2006 | Seguin et al. |
| 7,101,396 B2 | 9/2006 | Artof et al. |
| 7,175,656 B2 | 2/2007 | Khairkhahan |
| 7,201,772 B2 | 4/2007 | Schwammenthal et al. |
| 7,329,279 B2 | 2/2008 | Haug et al. |
| 7,351,256 B2 | 4/2008 | Hojeibane et al. |
| 7,374,573 B2 | 5/2008 | Gabbay |
| 7,429,269 B2 | 9/2008 | Schwammenthal et al. |
| 7,445,630 B2 | 11/2008 | Lashinski et al. |
| 7,510,575 B2 | 3/2009 | Spenser et al. |
| 7,585,321 B2 | 9/2009 | Cribier |
| 7,625,403 B2 | 12/2009 | Krivoruchko |
| 7,682,380 B2 | 3/2010 | Thornton et al. |
| 7,748,389 B2 | 7/2010 | Salahieh et al. |
| 7,758,632 B2 | 7/2010 | Hojeibane et al. |
| 7,780,726 B2 | 8/2010 | Seguin |
| 7,785,341 B2 | 8/2010 | Forster et al. |
| 7,837,727 B2 | 11/2010 | Goetz et al. |
| 7,942,927 B2 | 5/2011 | Kaye et al. |
| 7,955,377 B2 | 6/2011 | Melsheimer |
| 8,048,138 B2 | 11/2011 | Sullivan et al. |
| 8,048,153 B2 | 11/2011 | Salahieh et al. |
| 8,062,355 B2 | 11/2011 | Figulla et al. |
| 8,070,708 B2 | 12/2011 | Rottenberg et al. |
| 8,070,800 B2 | 12/2011 | Lock et al. |
| 8,118,866 B2 | 2/2012 | Herrmann et al. |
| 8,142,496 B2 | 3/2012 | Berreklouw |
| 8,167,935 B2 | 5/2012 | McGuckin, Jr. et al. |
| 8,182,528 B2 | 5/2012 | Salahieh et al. |
| 8,267,988 B2 | 9/2012 | Hamer et al. |
| 8,337,541 B2 | 12/2012 | Quadri et al. |
| 8,343,213 B2 | 1/2013 | Salahieh et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,449,599 B2 | 5/2013 | Chau et al. |
| 8,454,686 B2 | 6/2013 | Alkhatib |
| 8,545,544 B2 | 10/2013 | Spenser et al. |
| 8,551,161 B2 | 10/2013 | Dolan |
| 8,579,964 B2 | 11/2013 | Lane et al. |
| 8,585,755 B2 | 11/2013 | Chau et al. |
| 8,628,569 B2 | 1/2014 | Benichou et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,679,174 B2 | 3/2014 | Ottma et al. |
| 8,685,086 B2 | 4/2014 | Navia et al. |
| 8,728,155 B2 | 5/2014 | Montorfano et al. |
| 8,784,472 B2 | 7/2014 | Eidenschink |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,894,702 B2 | 11/2014 | Quadri et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,998,982 B2 | 4/2015 | Richter et al. |
| 9,005,273 B2 | 4/2015 | Salahieh et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,050,188 B2 | 6/2015 | Schweich, Jr. et al. |
| 9,072,603 B2 | 7/2015 | Tuval et al. |
| 9,125,740 B2 | 9/2015 | Morriss et al. |
| 9,155,619 B2 | 10/2015 | Liu et al. |
| 9,226,839 B1 | 1/2016 | Kariniemi et al. |
| 9,241,790 B2 | 1/2016 | Lane et al. |
| 9,301,836 B2 | 4/2016 | Buchbinder et al. |
| D755,384 S | 5/2016 | Pesce et al. |
| 9,326,852 B2 | 5/2016 | Spenser |
| 9,345,573 B2 | 5/2016 | Nyuli et al. |
| 9,421,098 B2 | 8/2016 | Gifford, III et al. |
| 9,480,559 B2 | 11/2016 | Vidlund et al. |
| 9,498,332 B2 | 11/2016 | Hacohen et al. |
| 9,532,870 B2 | 1/2017 | Cooper et al. |
| 9,554,897 B2 | 1/2017 | Lane et al. |
| 9,629,716 B2 | 4/2017 | Seguin |
| 2001/0056295 A1 | 12/2001 | Solem |
| 2002/0032481 A1 | 3/2002 | Gabbay |
| 2002/0099436 A1 | 7/2002 | Thornton et al. |
| 2004/0122503 A1 | 6/2004 | Campbell et al. |
| 2004/0143315 A1 | 7/2004 | Bruun et al. |
| 2004/0249433 A1 | 12/2004 | Freitag |
| 2004/0260394 A1 | 12/2004 | Douk et al. |
| 2005/0038494 A1 | 2/2005 | Eidenschink |
| 2005/0080430 A1 | 4/2005 | Wright et al. |
| 2005/0137688 A1 | 6/2005 | Salahieh et al. |
| 2005/0137697 A1 | 6/2005 | Salahieh et al. |
| 2005/0154443 A1 | 7/2005 | Linder et al. |
| 2005/0182483 A1 | 8/2005 | Osborne et al. |
| 2005/0240200 A1 | 10/2005 | Bergheim |
| 2006/0015171 A1 | 1/2006 | Armstrong |
| 2006/0020333 A1 | 1/2006 | Lashinski et al. |
| 2006/0089627 A1 | 4/2006 | Burnett et al. |
| 2006/0161250 A1 | 7/2006 | Shaw |
| 2006/0178700 A1 | 8/2006 | Quinn |
| 2006/0212111 A1 | 9/2006 | Case et al. |
| 2006/0259137 A1 | 11/2006 | Artof et al. |
| 2006/0271166 A1 | 11/2006 | Thill et al. |
| 2007/0055340 A1 | 3/2007 | Pryor |
| 2007/0198077 A1 | 8/2007 | Cully et al. |
| 2007/0213813 A1 | 9/2007 | Von Segesser et al. |
| 2008/0082083 A1 | 4/2008 | Forde et al. |
| 2008/0082166 A1 | 4/2008 | Styrc et al. |

(56) References Cited

U.S. PATENT DOCUMENTS

| | | |
|---|---|---|
| 2008/0097595 A1 | 4/2008 | Gabbay |
| 2008/0140003 A1 | 6/2008 | Bei et al. |
| 2008/0167705 A1 | 7/2008 | Agnew |
| 2008/0234814 A1 | 9/2008 | Salahieh et al. |
| 2008/0265680 A1 | 10/2008 | Hoffman et al. |
| 2008/0294234 A1 | 11/2008 | Hartley et al. |
| 2009/0005863 A1 | 1/2009 | Goetz et al. |
| 2009/0112159 A1 | 4/2009 | Slattery et al. |
| 2009/0248143 A1 | 10/2009 | Laham |
| 2009/0299449 A1 | 12/2009 | Styrc |
| 2009/0306768 A1 | 12/2009 | Quadri |
| 2010/0049313 A1 | 2/2010 | Alon et al. |
| 2010/0076548 A1 | 3/2010 | Konno |
| 2010/0161036 A1 | 6/2010 | Pintor et al. |
| 2010/0234940 A1 | 9/2010 | Dolan |
| 2011/0004296 A1 | 1/2011 | Lutter et al. |
| 2011/0071626 A1 | 3/2011 | Wright et al. |
| 2011/0077730 A1 | 3/2011 | Fenster |
| 2011/0137397 A1 | 6/2011 | Chau et al. |
| 2011/0224785 A1 | 9/2011 | Hacohen |
| 2011/0251678 A1 | 10/2011 | Eidenschink et al. |
| 2011/0282439 A1 | 11/2011 | Thill et al. |
| 2011/0319989 A1 | 12/2011 | Lane et al. |
| 2012/0123511 A1 | 5/2012 | Brown |
| 2012/0130473 A1 | 5/2012 | Norris et al. |
| 2012/0130474 A1 | 5/2012 | Buckley |
| 2012/0130475 A1 | 5/2012 | Shaw |
| 2012/0165915 A1 | 6/2012 | Melsheimer et al. |
| 2012/0179244 A1 | 7/2012 | Schankereli et al. |
| 2012/0296360 A1 | 11/2012 | Norris et al. |
| 2012/0310328 A1 | 12/2012 | Olson et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0297013 A1 | 11/2013 | Klima et al. |
| 2013/0310928 A1 | 11/2013 | Morriss et al. |
| 2013/0331929 A1 | 12/2013 | Mitra et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0046430 A1 | 2/2014 | Shaw |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0148891 A1 | 5/2014 | Johnson |
| 2014/0163690 A1 | 6/2014 | White |
| 2014/0172069 A1 | 6/2014 | Roeder et al. |
| 2014/0188210 A1 | 7/2014 | Beard et al. |
| 2014/0188221 A1 | 7/2014 | Chung et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0257467 A1 | 9/2014 | Lane et al. |
| 2014/0257475 A1 | 9/2014 | Gross et al. |
| 2014/0277358 A1 | 9/2014 | Slazas |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358224 A1 | 12/2014 | Tegels et al. |
| 2014/0379065 A1 | 12/2014 | Johnson et al. |
| 2014/0379076 A1 | 12/2014 | Vidlund et al. |
| 2015/0045881 A1 | 2/2015 | Lim |
| 2015/0094802 A1 | 4/2015 | Buchbinder et al. |
| 2015/0127097 A1 | 5/2015 | Neumann et al. |
| 2015/0142103 A1 | 5/2015 | Vidlund |
| 2015/0173897 A1 | 6/2015 | Raanani et al. |
| 2015/0272730 A1 | 10/2015 | Melnick et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2016/0106539 A1 | 4/2016 | Buchbinder et al. |
| 2016/0213473 A1 | 7/2016 | Hacohen et al. |
| 2016/0242902 A1 | 8/2016 | Morriss et al. |
| 2016/0310268 A1 | 10/2016 | Oba et al. |
| 2016/0317301 A1 | 11/2016 | Quadri et al. |
| 2016/0324640 A1 | 11/2016 | Gifford, III et al. |
| 2016/0367360 A1 | 12/2016 | Cartledge et al. |
| 2016/0367368 A1 | 12/2016 | Vidlund et al. |

FOREIGN PATENT DOCUMENTS

| | | |
|---|---|---|
| WO | 2006/089236 A1 | 8/2006 |
| WO | 2007/059252 A1 | 5/2007 |
| WO | 2008/029293 A2 | 3/2008 |
| WO | 2006/070797 A2 | 6/2008 |
| WO | 2008/103722 A2 | 8/2008 |
| WO | 2009/091509 A1 | 7/2009 |
| WO | 2012/024428 A2 | 2/2012 |
| WO | 2012/127309 A1 | 9/2012 |
| WO | 2013/059747 A1 | 4/2013 |
| WO | 2013/078497 A1 | 6/2013 |
| WO | 2014/022124 A1 | 2/2014 |
| WO | 2014/076696 A1 | 5/2014 |
| WO | 2014/145338 A1 | 9/2014 |
| WO | 2014/164364 A1 | 10/2014 |
| WO | 2016/093877 A1 | 6/2016 |

OTHER PUBLICATIONS

Extended European Search Report dated Jun. 29, 2017; Appln. 11809374.9.

Saturn Project; "A Novel Solution for Transcatheter Heart Valve Replacement Specifcally Designed to Address Clinical Therapeutic Needs on Mitral Valve", 8 pages, Dec. 2016.

Georg Lutter, et al; "Percutaneous Valve Replacement: Current State and Future Prospects", The Annals of Thoracic Surgery; vol. 78, pp. 2199-2206; Dec. 2004.

Dusan Pavcnik Md, et al; "Developoment and Initial Experimental Evaluation of a Prosthetic Aortic Valve for Transcatheter Placement", Cardiovascular Radiology Apr. 1992, vol. 183, pp. 151-154.

Righini Presentation EUROPCR May 2015 (Saturn)-(downloaded from: https://www.pcronline.com/Cases-resourcesimages/Resouces/Course-videos-slides/2015/Cardiovascularinnovation-pipeline-Mitral-and-triscuspid-valve-interventions).

UK Office Action dated Feb. 8, 2017; Appln. No. 1613219.3.

IPRP dated May 19, 2015; PCT/IL2013/050937.

ISR/WO dated Mar. 17, 2014; PCT/IL2013/050937.

ISR/WO dated Oct. 27, 2015; PCT/IL2015/050792.

ISR/WO dated May 30, 2016; PCT/IL2015/050125.

USPTO Corrected Notice of Allwance dated Dec. 13, 2013 in connection with U.S. Appl. No. 13/675,119.

USPTO NFOA dated Jan. 18, 2017 in connection with U.S. Appl. No. 14/626,267.

USPTO NFOA dated Jan. 21, 2016 in connection with U.S. Appl. No. 14/237,264.

USPTO NFOA dated Feb. 7, 2017 in connection with U.S. Appl. No. 14/689,608.

(56) References Cited

OTHER PUBLICATIONS

USPTO NFOA dated Jul. 1, 2016 in connection with U.S. Appl. No. 14/161,921.
USPTO NFOA dated Nov. 27, 2015 in connection with U.S. Appl. No. 14/626,267.
USPTO NFOA dated Dec. 10, 2015 in connection with U.S. Appl. No. 14/237,258.
USPTO NOA dated Jul. 1, 2016 in connection with U.S. Appl. No. 14/442,541.
USPTO NOA dated Sep. 29, 2016 in connection with U.S. Appl. No. 14/442,541.
USPTO NOA dated Oct. 16, 2013 in connection with U.S. Appl. No. 13/675,119.
USPTO RR dated Jan. 20, 2016 in connection with U.S. Appl. No. 14/161,921.

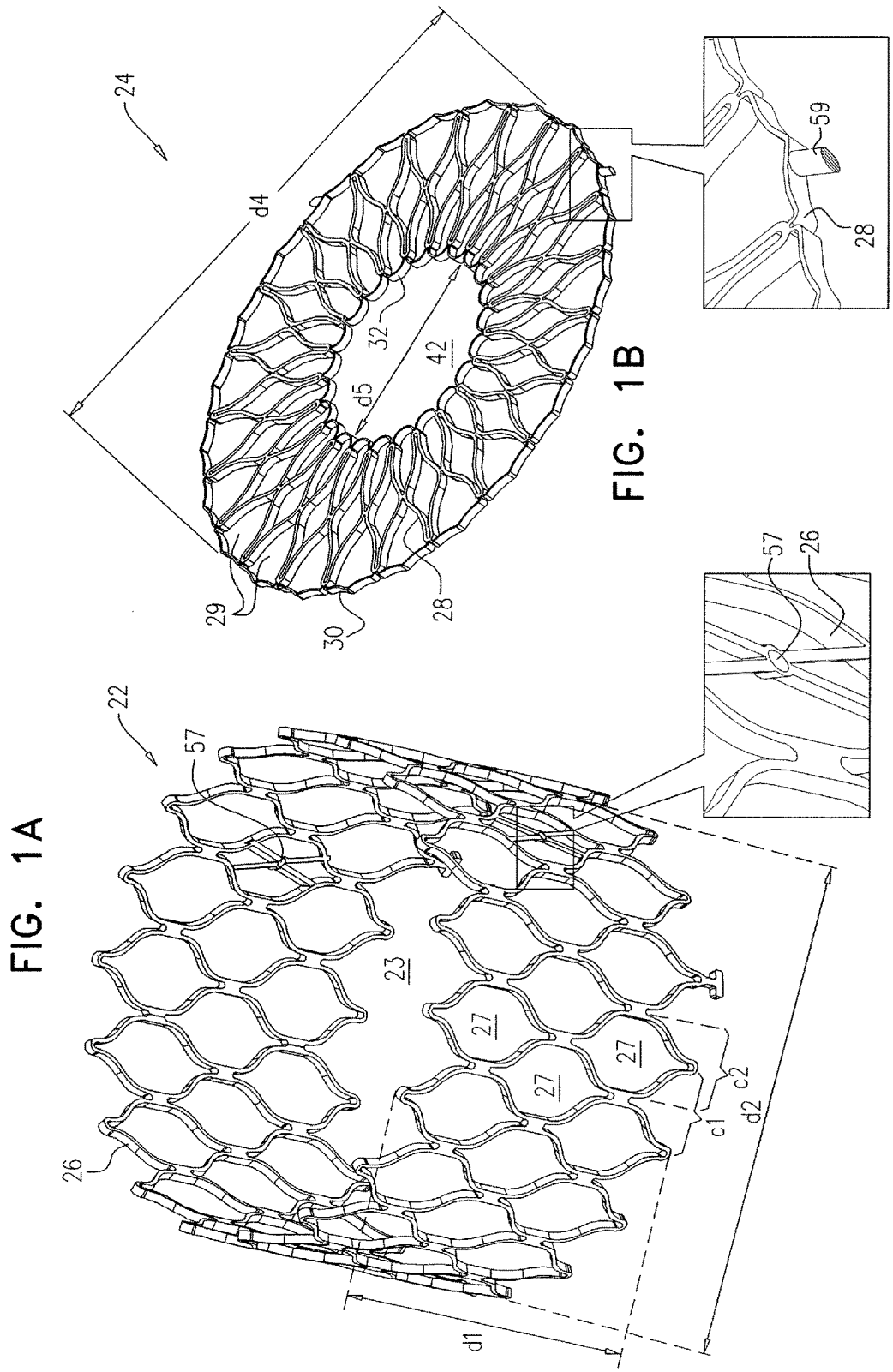

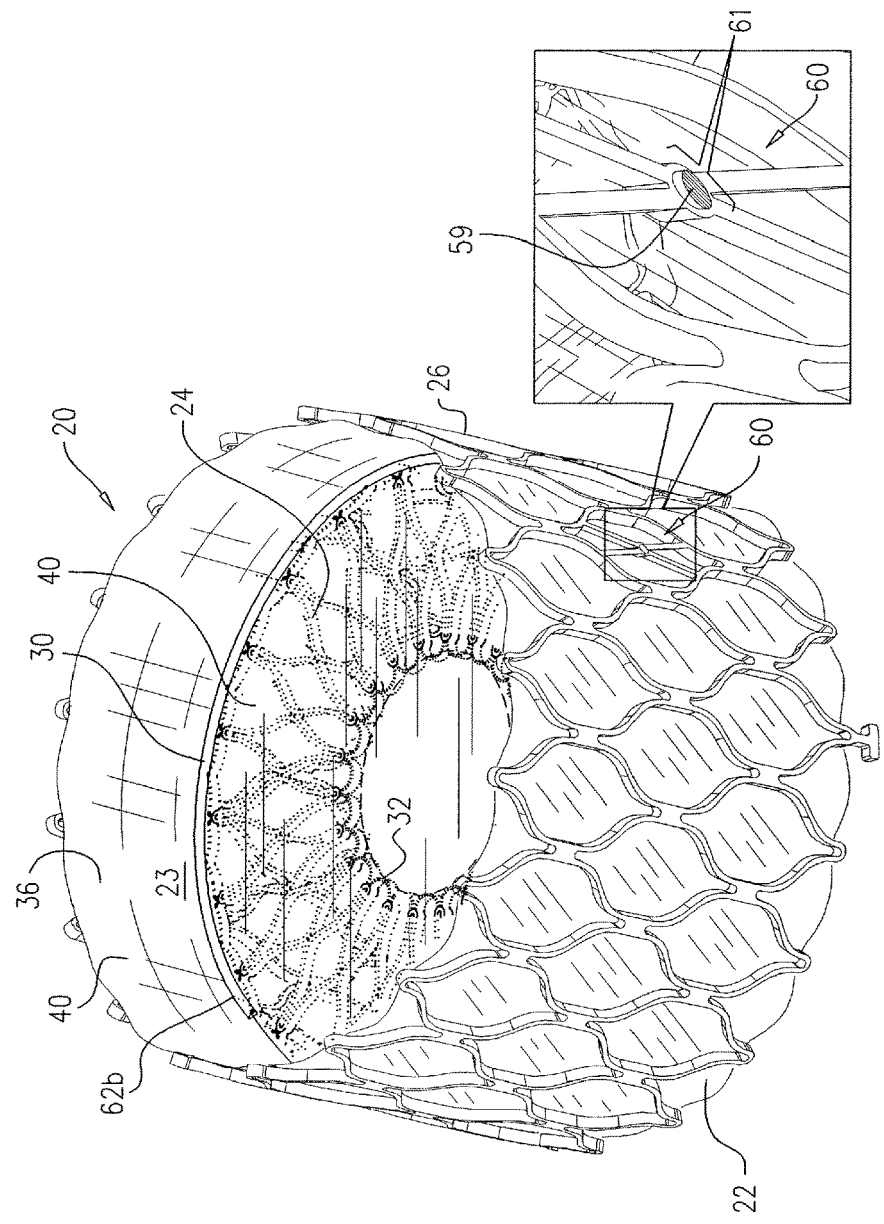
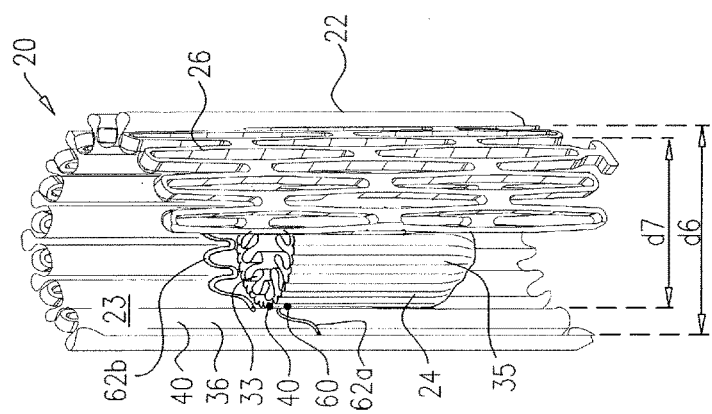
FIG. 1C
FIG. 1D

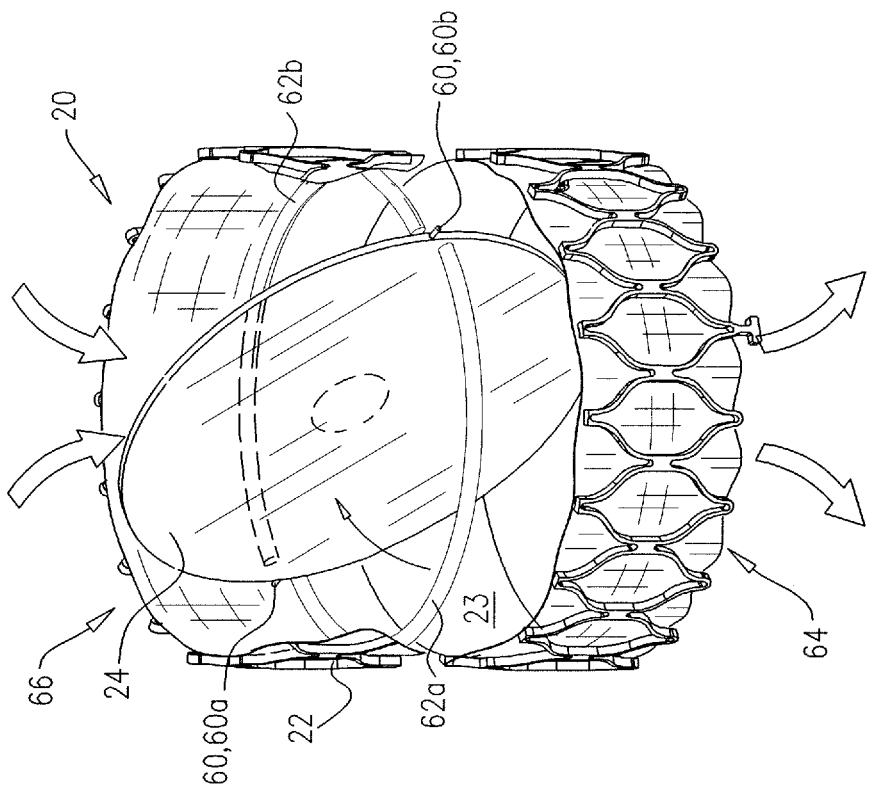
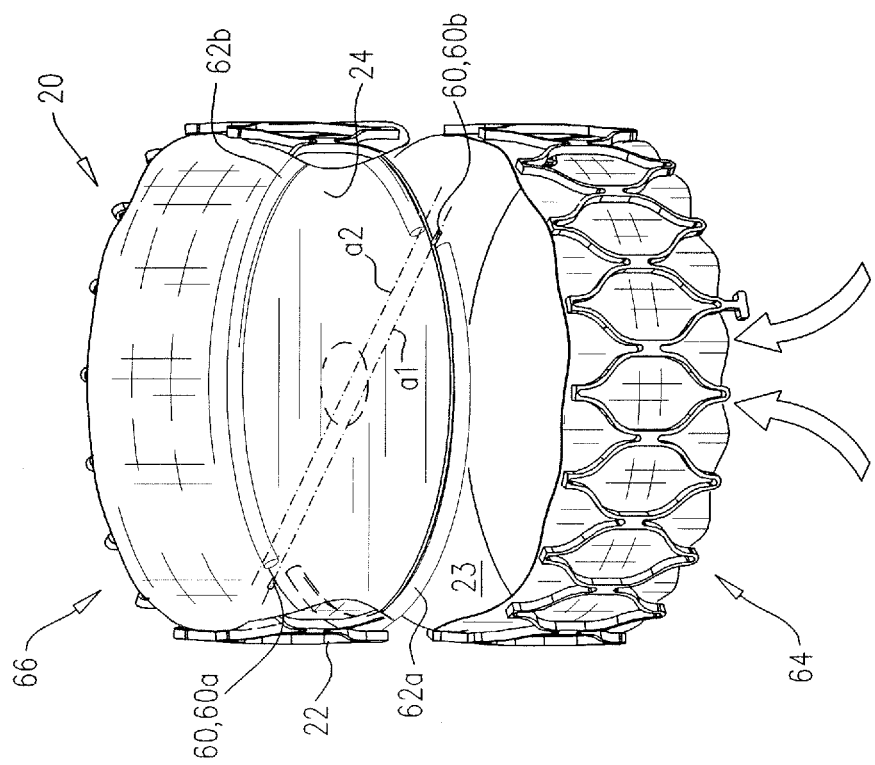

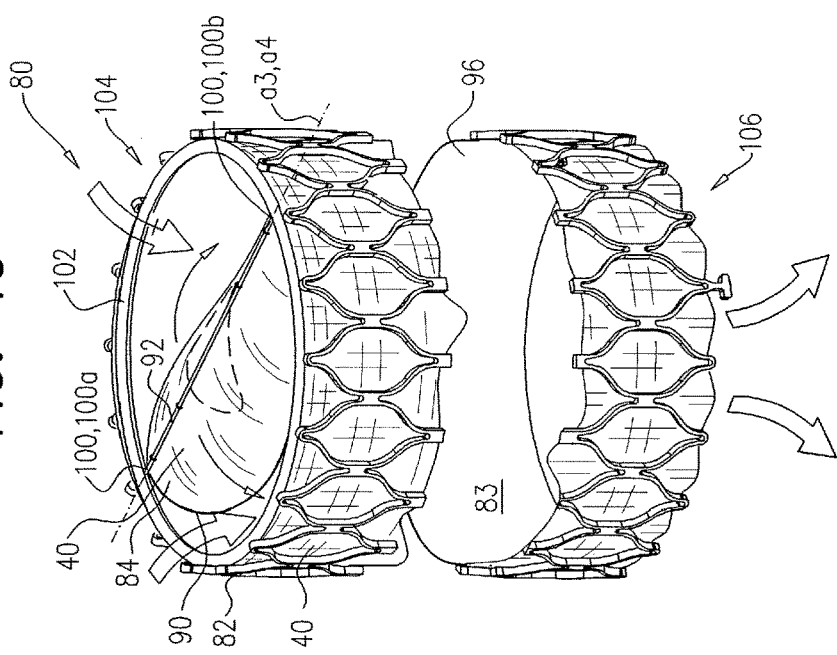
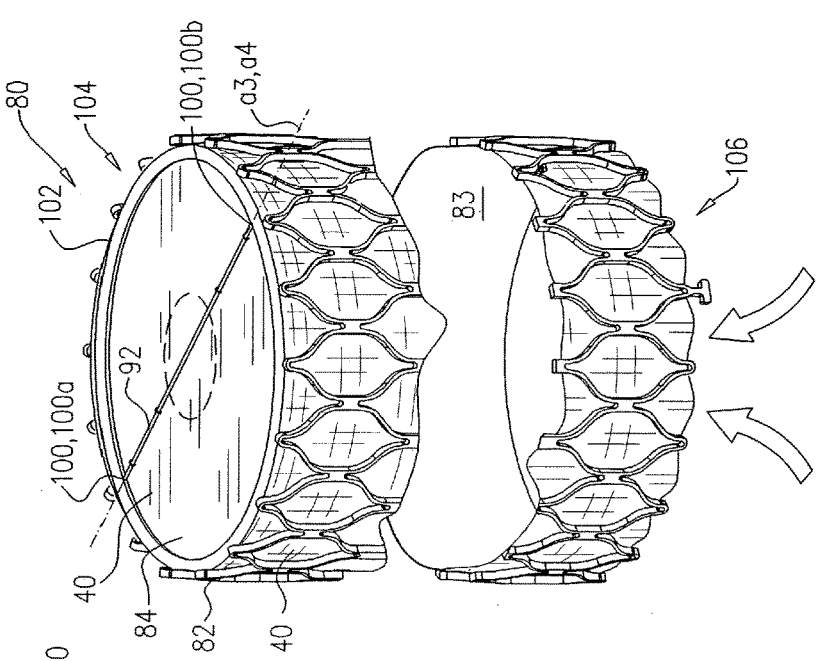
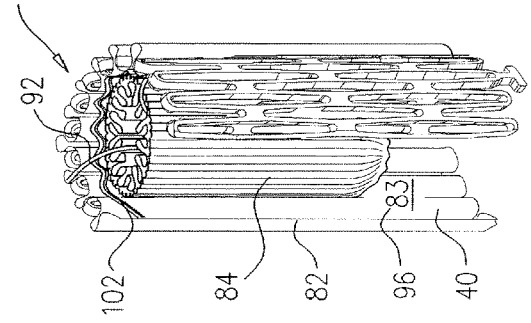

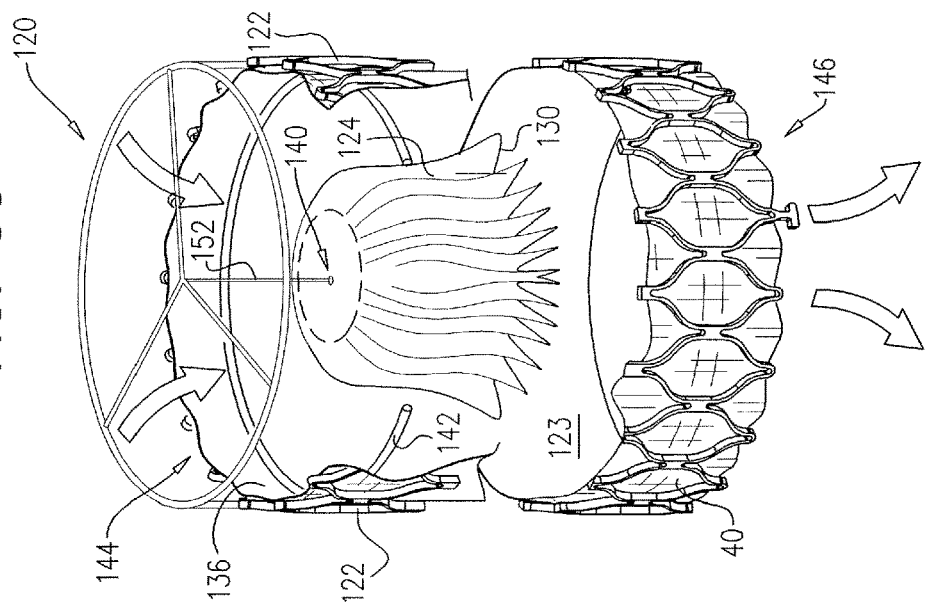
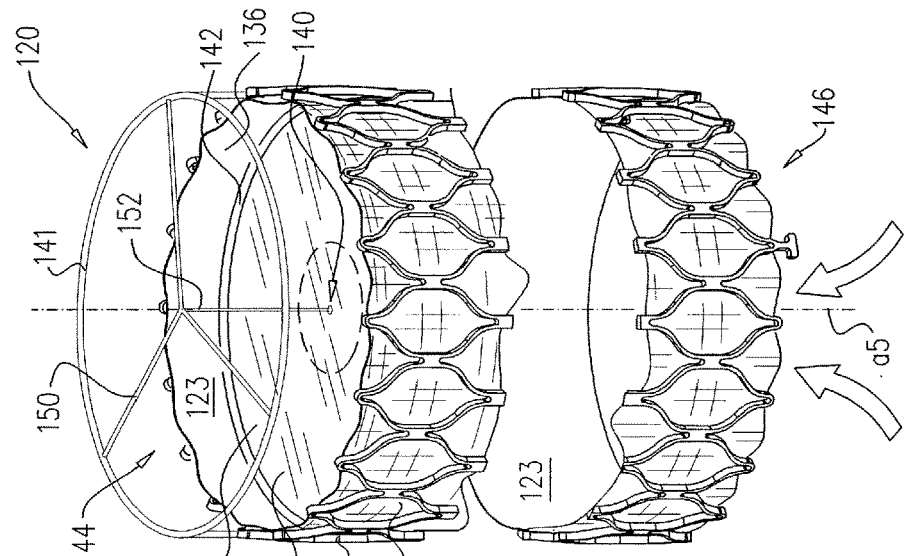
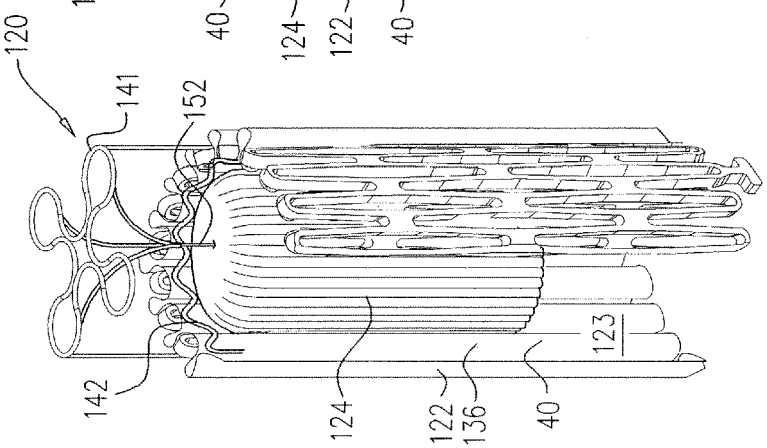

PERCUTANEOUSLY-DELIVERABLE MECHANICAL VALVE

CROSS-REFERENCES TO RELATED APPLICATIONS

The present application is a Continuation of U.S. Ser. No. 14/442,541 to HaCohen et al., entitled "Percutaneously-deliverable mechanical valve," which published as US 2016/0213473, and which issued as U.S. Pat. No. 9,498,332; which is the US National Phase of PCT IL2013/050937 to HaCohen et al, entitled "Percutaneously-deliverable mechanical valve," which published as WO 2014/076696; which is a Continuation of U.S. patent application Ser. No. 13/675,119 to HaCohen et al., entitled "Percutaneously-deliverable mechanical valve," filed on Nov. 13, 2012, which is incorporated herein by reference, and which issued as U.S. Pat. No. 8,628,571.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

A percutaneously-deliverable (e.g., transluminally-deliverable) mechanical prosthetic valve, comprising a tubular element and a valve member is described. Typically, the tubular element and valve member are restrained in respective compressed configurations for delivery, and automatically expand into respective expanded configurations when released at the native valve.

There is therefore provided, in accordance with an application of the present invention, apparatus for regulating blood flow of a subject, the apparatus including a prosthetic valve, the prosthetic valve:
including:
a tubular element, shaped to define a lumen therethrough, and
a valve member, configured to be coupled to the tubular element and to be disposed within the lumen, and having:
a compressed configuration in which the lumen has a compressed width, the valve member is generally cylindrical, and the prosthetic valve is configured to be percutaneously delivered into the subject, and
an expanded configuration in which:
the lumen has an expanded width that is greater than the compressed width, and
the valve member is generally disc-shaped, is coupled to the tubular element, and is disposed within the lumen.

In an application, the prosthetic valve is configured to function as a check valve when in the expanded configuration thereof, and not when in the compressed configuration thereof.

In an application, in the compressed configuration, the valve member is coupled to the tubular element.

In an application, in the compressed configuration, the valve member is disposed within the lumen.

In an application:
the lumen has a first end and a second end, and
the valve member, when the valve is in the expanded configuration thereof:
has an open state, in which the first and second ends of the lumen are in fluid communication with each other,
has a closed state, in which the first and second ends of the lumen are generally not in fluid communication with each other, and
is movable between the open and closed states.

In an application, in the expanded configuration, the valve member is configured to move between the open and closed states in response to changes in relative pressure between the first and second ends of the lumen.

In an application, in the expanded configuration, the valve member, in at least the closed state thereof, has a diameter that is no more than 20 percent smaller than the expanded width of the lumen.

In an application, the valve member has a compressed diameter in the compressed configuration of the prosthetic valve, and an expanded diameter in the in the expanded configuration of the prosthetic valve, and the expanded diameter is at least twice as great as the compressed diameter.

In an application, in the expanded configuration, the prosthetic valve is configured to act as a check valve.

In an application, in the expanded configuration, the valve member is configured to move toward the open state when pressure at the first end of the lumen is greater than pressure at the second end of the lumen, and to move toward the closed state when pressure at the second end of the lumen is greater than pressure at the first end of the lumen.

In an application, the valve member is coupled to the tubular element at at least two coupling points, the coupling points defining an axis therebetween.

In an application, the valve member is configured to move between the open and closed states thereof, by rotating around the axis between the coupling points.

In an application, the valve member is configured to move between the open and closed states thereof, by deflecting around the axis between the coupling points.

In an application, the apparatus further includes a coupling rod, coupled to the coupling points, and coupled to the valve member along the axis between the coupling points, and the valve member is configured to move between the open and closed states thereof, by bending around the coupling rod.

In an application, the prosthetic valve includes a coupling element that includes at least one strut, the strut being coupled to the tubular element, and to the valve member at a coupling point that is generally midway across a diameter of the valve member, and the valve member is configured to move between the open and closed states by deflecting from the coupling point.

In an application, the valve member is configured to move between the open and closed states by collapsing and expanding.

In an application, the valve member is configured to move between the open and closed states thereof without changing a shape thereof.

In an application, the prosthetic valve is configured such that, when the valve member moves toward the open state, at least part of the valve member moves toward the first end of the lumen and at least part of the valve member moves toward the second end of the lumen.

In an application, the valve member is configured to move between the open and closed states thereof by changing a shape thereof.

In an application, the valve member is configured to be biased toward being in the closed state thereof.

In an application, in the compressed configuration, the prosthetic valve has a greatest transverse diameter of less than 12 mm.

In an application, in the compressed configuration, the prosthetic valve has a greatest transverse diameter of less than 9 mm.

In an application, in the compressed configuration, the prosthetic valve has a greatest transverse diameter of less than 6 mm.

In an application, the prosthetic valve is intracorporeally expandable from the compressed configuration to the expanded configuration.

In an application, the prosthetic valve is configured to be percutaneously delivered in the constrained configuration thereof, by being restrained in the compressed configuration during the percutaneous delivery, and the prosthetic valve is configured to automatically expand toward the expanded configuration thereof when no longer restrained.

The present invention will be more fully understood from the following detailed description of applications thereof taken together with the drawings, in which:

BRIEF DESCRIPTION OF THE DRAWINGS

FIGS. 1A-D are schematic illustrations of a prosthetic valve, comprising a tubular element and a valve member, in accordance with some applications of the invention;

FIGS. 3A-B are schematic illustrations of a prosthetic valve in open and closed states thereof, in accordance with some applications of the invention;

FIGS. 4A-C are schematic illustrations of a prosthetic valve, comprising a tubular element and a valve member, in accordance with some applications of the invention; and FIGS. 5A-C are schematic illustrations of a prosthetic valve comprising a tubular element and a valve member, in accordance with some applications of the invention.

DETAILED DESCRIPTION OF EMBODIMENTS

Figure 2B:
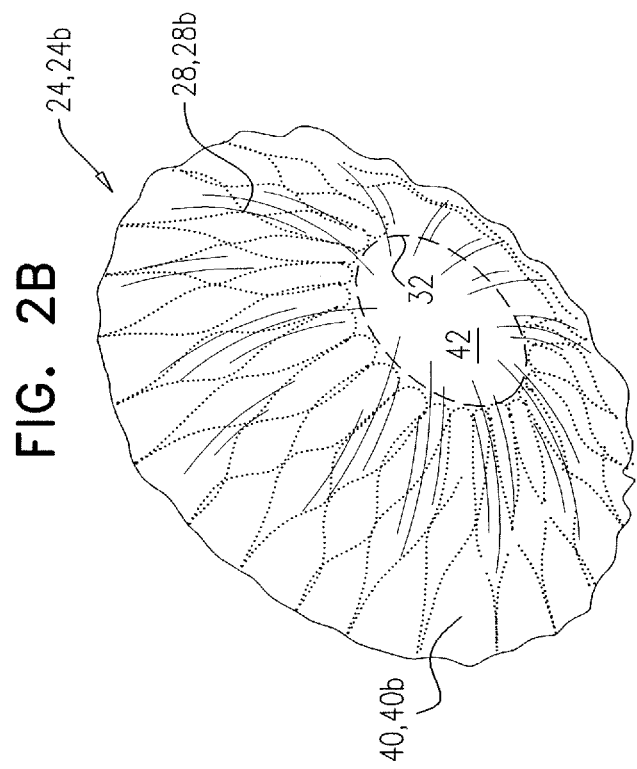
FIGS. 2A-B are schematic illustrations of the valve member, in accordance with respective applications of the invention.

Reference is made to FIGS. 1A-D, which are schematic illustrations of a prosthetic valve 20, comprising a tubular element 22 and a valve member 24, in accordance with some applications of the invention. It is to be noted that throughout this application, including the specification and the claims, the term "valve member" is defined as the movable obstruction (e.g., inside the tubular element) that restricts and/or controls flow through the valve, as is known in the general valve art. Prosthetic valve 20 is configured to be placed in a lumen of the body of the subject, such as in a blood vessel and/or at a native valve of the subject. Typically, prosthetic valve 20 is configured to be placed at a native heart valve of a subject, and to replace native functionality of the native valve. FIG. 1A shows tubular element 22 alone, FIG. 1B shows valve member 24 alone, FIG. 1C shows valve 20 in a compressed configuration thereof, and FIG. 1D shows valve 20 in an expanded configuration thereof, in accordance with some applications of the invention.

FIG. 1A shows tubular element 22, in an expanded configuration thereof, in accordance with some applications of the invention. Tubular element 22 is shaped to define a lumen 23 therethrough, and has a length d1 along a longitudinal axis of the tubular element, from a first end of the lumen to a second end of the lumen (e.g., from a first end of element 22 to a second end of element 22). Lumen 23 is defined by an inner surface 36 (FIG. 1D) of tubular element 22, and has a width d2. That is, d2 represents an inner width of tubular element 22. Typically, tubular element 22 is generally cylindrical (i.e., element 22 has a generally circular transverse cross-section), and width d2 represents a diameter of lumen 23. Alternatively, tubular element 22 has a transverse cross-section that is not generally circular, and width d2 represents a maximum width of lumen 23.

Typically, length d1 is greater than 10 mm and/or less than 30 mm (e.g., 10-30 mm). Typically, width d2 is greater than 20 mm and/or less than 40 mm (e.g., 20-40 mm, such as 30 mm). That is, in the expanded configuration thereof (as shown in FIG. 1A), tubular element 22 has length of greater than 10 mm and/or less than 30 mm, and an inner width of greater than 20 mm and/or less than 40 mm.

Typically, tubular member 22 comprises a frame 26 that defines a circumferentially-repeating arrangement of cells 27. Typically, frame 26 defines, along length d1, longitudinal columns c1 comprising one cell 27, alternating with longitudinal columns c2 comprising two cells. Typically, frame 26 defines circumferential rows comprising more than 10 and/or less than 25 cells 27 (e.g., 18 cells). It is to be noted, however, that the scope of the invention includes other configurations of frame 26.

FIG. 1B shows valve member 24, in an expanded configuration thereof, in accordance with some applications of the invention. Valve member 24 typically has a shape that is similar to that of lumen 23 of tubular element 22. That is, a transverse cross-section of valve member 24 typically has a shape that is similar to the shape of the transverse cross-section of lumen 23. For example, for applications in which tubular element 22 is generally cylindrical, valve member 24 typically has a generally disc-shaped transverse cross-section. For such applications, other dimensions and/or shapes of valve member 24 may vary (e.g., as described with reference to FIGS. 2A-B).

Typically, valve member 24 has a width d4 that is no more than 20% smaller than width d2 of tubular element 22 (e.g., no more than 10% smaller, such as no more than 5% smaller). For applications in which tubular element 22 is generally cylindrical and valve member is generally disc-shaped, widths d3 and d4 represent transverse cross-sectional diameters of lumen 23 and valve member 24, respectively, and the diameter of valve member 24 is typically no less than 20% smaller than the diameter of lumen 23 (i.e., no less than 20% smaller than the inner diameter of tubular element 22). Thereby, width d4 is typically greater than 20 mm and/or less than 40 mm (e.g., 20-40 mm, such as 30 mm).

Typically, valve member 24 comprises a frame 28 that defines an outer edge 30, an inner edge 32, and a radially-repeating arrangement of cells 29, disposed between the inner and outer edges. Inner edge 32 defines an opening 42, the presence of which facilitates compression of valve member 24 into the compressed configuration thereof (e.g., as described with reference to FIG. 1C). That is, the absence of frame material at opening 42 facilitates compression of the valve member into a generally cylindrical shape. Typically, opening 42 has a width d5 (e.g., a diameter) of more than 5 mm and/or less than 20 mm (e.g., between 5 and 20 mm, such as 12 mm). Alternatively or additionally, frame 28 may comprise a portion of increased flexibility, e.g., instead of defining opening 42.

For clarity, FIGS. 1A-B show frames 26 and 28 of tubular element 22 and valve member 24, respectively. However, tubular element 22 and valve member 24 comprise a covering 40, e.g., as shown in FIGS. 1C-D. Covering 40 covers at least part of frames 26 and 28. Non-limiting examples of materials that covering 40 may comprise, include cotton and polymers (e.g., polyester). Typically the covering has a thickness that is less than 1 mm (e.g., between 0.05 mm and 0.6 mm).

FIG. 1C shows valve 20 in the compressed configuration thereof, in which valve member 24, in a compressed configuration thereof, is disposed within lumen 23 of tubular element 22, in the compressed configuration thereof. FIG. 1D shows valve 20 in the expanded configuration thereof, in which valve member 24, in an expanded configuration thereof, is disposed within lumen 23 of tubular element 22, in an expanded configuration thereof.

Valve 20 is configured to be percutaneously (e.g., transcatheterally and/or transluminally, such as transfemorally) delivered to the native heart valve of a subject, by being compressed (e.g., "crimped") into the compressed configuration thereof (i.e., a delivery configuration thereof). Valve 20 is typically configured to be restrained in the compressed configuration (e.g., by an overtube) during delivery of the valve, and to automatically move into an expanded configuration when released (e.g., by being deployed from the overtube). Typically, frames 26 and 28 comprise a shape-memory material such as, but not limited to, nitinol, which facilitates this automatic expansion.

Covering 40 typically covers inner surface 36 of cylindrical element 22 and at least one side of valve member 24, including opening 42. Opening 42 is thereby an opening in frame 28 but typically not an opening in covering 40, and thereby typically not an opening through the entire of valve member 24 (FIG. 1D).

As described hereinabove, tubular element 22 is typically generally cylindrical. That is, element 22 is typically generally cylindrical in the expanded configuration thereof. Tubular element 22 is typically also generally cylindrical in the compressed configuration thereof. In the compressed configuration thereof, tubular element 22 (e.g., lumen 23 thereof) has a width d6 (e.g., a diameter) that is smaller than width d2 of the tubular element in the compressed configuration thereof. Typically, width d2 is more than 1.5 times (e.g., more than 4 times) greater than width d6.

As described hereinabove, valve member 24 is typically generally disc-shaped. That is, member 24 is typically generally disc-shaped in the expanded configuration thereof. In the compressed configuration thereof, valve member 24 is typically elongate, such as generally cylindrical, and has a width (e.g., a diameter) d7. Typically, width d4 (FIG. 1B) is more than twice (e.g., more than 5 times, such as more than 10 times) greater than width d7. Typically, when valve member 24 moves from the compressed configuration to the expanded configuration, (1) a first end 33 of the cylinder defined by valve member 24 in the compressed configuration, expands to define outer edge 30 of the valve member in the expanded configuration, and a second end 35 of the cylinder expands to define inner edge 32. It is to be noted that covering 40 covers opening 42 in frame 28, and therefore inner edge 32 is an inner edge of frame 28, and does not define an opening through the entire of valve member 24.

Valve member 24 is typically disposed in lumen 23 of tubular element 22, in both the compressed configuration and the expanded configuration of valve 20. Valve member 24 is coupled to tubular element 22 at one or more (e.g., two) coupling points 60. Coupling points 60 comprise a coupling element 61, which may comprise a hinge, a connector (e.g., a connecting wire or suture), or any other suitable coupling element. For some applications, and as shown in FIG. 1D, coupling element 61 comprises a hinge formed by a protrusion 59 of frame 28 protruding into a slot 57 defined by frame 26. Typically, and as described in more detail with reference to FIGS. 3A-B, valve 20 further comprises one or more valve seats 62, configured to facilitate sealing between tubular element 22 and valve member 24.

Typically, width d6 is greater than 2 mm and/or less than 12 mm (e.g., 2-10 mm, such as 3-6 mm). Typically, width d7 is greater than 2 mm and/or less than 10 mm (e.g., 2-8 mm, such as 2-6 mm). Typically, valve member 24 is configured to be compressible such that width d7 is smaller than width d6 in a maximally-compressed configuration of cylindrical element 22, e.g., such that cylindrical element 22 is compressible to generally the same width in the presence or absence of valve member 24.

As described hereinabove, prosthetic valve 20 is configured to be placed (i.e., implanted) at a native heart valve of a subject, and to replace native functionality of the native valve. Prosthetic valve 20 is configured to act as a one-way valve (e.g., a check valve). That is, prosthetic valve 20 is configured to generally allow blood to flow in a first direction through lumen 23 of tubular element 22, and to inhibit blood from flowing in a second direction through the lumen. Typically, prosthetic valve 20 resembles and/or is configured to act as a "tilting disc" valve, as is known in the valve art. Valve member 24, disposed in lumen 23 of tubular element 22, provides valve functionality by being configured to move between an open state and a closed state in response to changes in relative pressure between each end of the lumen of tubular element 22 (i.e., in response to changes in relative pressure between blood at each end of the lumen; e.g., as described hereinbelow with reference to FIGS. 3A-B). Movement of valve member 24 between the open and closed states thereof, thereby moves prosthetic valve 20 between open and closed states thereof.

Figure 2A:
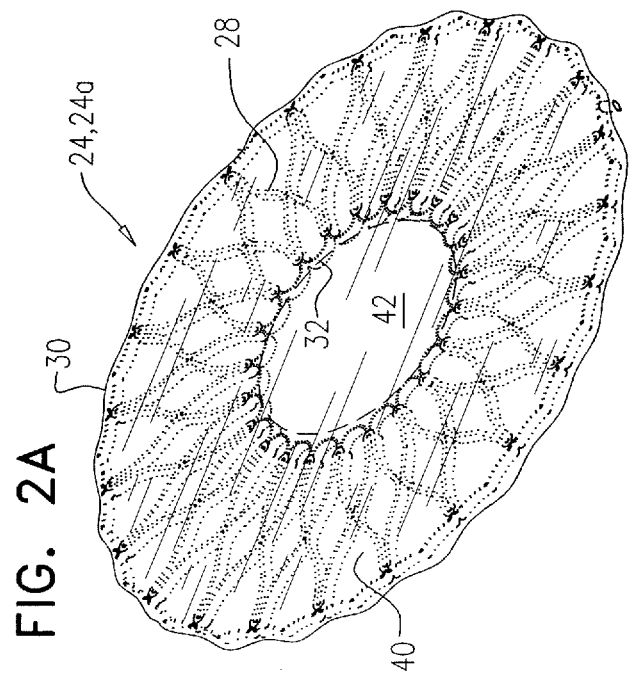

Reference is made to FIGS. 2A-B, which are schematic illustrations of valve member 24, in accordance with respective applications of the invention. As described hereinabove, valve member 24 is typically disc-shaped in the expanded configuration thereof. FIG. 2A shows valve member 24, comprising a disc-shaped valve member 24*a* in the expanded configuration thereof, in accordance with some applications of the invention. As described hereinabove, frame 28 and opening 42 of valve member 24 are typically covered in covering 40.

For some applications, valve member 24 has a shape that is different to a flat disc. FIG. 2B shows valve member 24, comprising a frustoconical valve member 24*b* in the expanded configuration thereof, in accordance with some applications of the invention. For some applications of the invention, frame 28 of valve member 24b comprises a frame 28b, which is configured to assume a frustoconical shape. For some applications of the invention, covering 40 of valve member 24b comprises a covering 40b, which is configured to facilitate the valve member assuming the frustoconical shape, e.g., by restricting full expansion of the frame. For some such applications, valve member 24b comprises frame 28 (i.e., the same frame as member 24a), and the assuming of the frustoconical shape of valve member 24b is facilitated mainly (e.g., solely) by covering 40b.

It is to be noted that FIGS. 2A-B show non-limiting examples of possible shapes of valve member 24, and that the scope of the invention includes valve member 24 having other shapes. Similarly, it is to be noted that, although tubular element 22 is shown as being substantially cylindrical, the scope of the invention includes tubular element 22 having other shapes, e.g., so as to facilitate blood flow, so as to conform to the shape of the native valve, and/or so as to facilitate coupling to the native valve and/or to auxiliary apparatus, such as a prosthetic valve support, such as the prosthetic valve supports described in US 2012/0022640 to Gross et al., which is incorporated herein by reference. For example, tubular element 22 may comprise and/or define flared ends, barbs, clips, or any other such features, e.g., as are known in the art.

Reference is made to FIGS. 3A-B, which are schematic illustrations of functioning of valve 20, in accordance with respective applications of the invention. FIGS. 3A-B show valve member 24 as disc-shaped (e.g., as shown for valve member 24a, described with reference to FIG. 2A), but valve members of other shapes may be used, and typically function similarly, mutatis mutandis.

Valve member 24 is coupled to tubular element 22 at one or more coupling points 60, such that the valve member can rotate between (1) an open state in which the valve member generally allows fluid (e.g., blood) to flow through lumen 23, and (2) a closed state in which the valve member generally blocks lumen 23, thereby generally inhibiting fluid from flowing through the lumen. Typically, valve member 24 is coupled to tubular element 22 at two coupling points 60 (e.g., coupling points 60a and 60b), such that the valve member can rotate around an axis a1 between the two coupling points. Typically, valve member 24 does not change shape when moving between the open and closed states. FIG. 3A shows valve member 24 (and thereby valve 20) in the closed state thereof, and FIG. 3B shows valve member 24 (and thereby valve 20) in the open state thereof.

Typically, coupling points 60a and 60b do not lie on a central transverse axis a2 of tubular element 22. That is, axis a1 is typically a non-diameter chord of a transverse cross-section of tubular element 22. Such a configuration typically facilitates the functioning of valve 20 as a tilting-disc valve, as is known in the art.

Valve 20 is configured such that valve member 24 moves between the open state and the closed state in response to changes in relative fluid pressure between each end of lumen 23, and thereby valve 20 is configured to act as a one way valve (e.g., a check valve). In the open state, a first end 64 of tubular element 22 is in fluid communication with a second end 66 of the tubular element. In the closed state, fluid communication between the two ends is reduced, compared to in the open state (e.g., the first and second ends are substantially not in fluid communication).

As shown in FIG. 3A, when fluid pressure at a second end 66 of tubular member 22 is higher than fluid pressure at a first end 64 of the tubular member (e.g., when fluid "tries" to move from the second end to the first end), valve member 24 is in (e.g., moves into) the closed state, thereby inhibiting flow of the fluid from the second end to the first end. As shown in FIG. 3B, when fluid pressure at first end 64 is higher than fluid pressure at second end 66 (e.g., when fluid "tries" to move from the first end to the second end), valve member 24 moves into the open state, thereby facilitating flow of the fluid from the first end to the second end. Thereby, valve 20 acts as a check-valve (e.g., a tilting-disc valve), first end 64 is an upstream end of the valve, and second end 66 is a downstream end of the valve. It is to be noted that, when the valve member moves toward the open state, part of valve member 24 moves toward first end 64 (i.e., upstream), and part of the valve member moves toward second end 66 (i.e., downstream).

Valve member 24 is typically configured (e.g., dimensioned) such that, in the closed state, outer edge 30 (see FIG. 1B) of the valve member is positioned closely to the inner surface of tubular element 22 (e.g., the valve member is in close contact with the inner surface of the tubular element). For example, and as described hereinabove, the diameter of valve member 24 is typically no more than 20% smaller than the width of the lumen of the tubular element.

For some applications of the invention, valve 20 further comprises at least one valve seat 62, configured to facilitate contact (e.g., sealing) between valve member 24 and tubular element 22. For some such applications, and as shown in FIGS. 3A-B, seat 62 comprises two arc-shaped seats 62a and 62b that are disposed on the inner surface of the tubular element, and form respective arcs whose endpoints are adjacent to coupling points 60a and 60b. For example, and as shown in FIGS. 3A-B, (1) seat 62a forms a major arc between coupling points 60a and 60h, disposed slightly closer than coupling points 60 to first end 64, and (2) seat 62b forms a complementary minor arc, disposed slightly closer than coupling points 60 to second end 66.

Seats 62a and 62b protrude into lumen 23 of tubular element 22, so as to facilitate sealing between the tubular element and valve member 24. For some applications, the seats comprise a sealing element, such as a sealing surface, to further facilitate such sealing. Typically, the seats and/or sealing elements comprise a fabric, a resin and/or a polymer and are configured to fold, crumple, contract, and/or compress when valve 20 is compressed into the compressed configuration thereof, and to unfold, uncrumple, expand, and/or uncompress into the configuration shown in FIGS. 3A-B, when valve 20 is moved into the uncompressed configuration thereof. For example, the seats may comprise a fabric, sutured to frame 26, and configured to crumple and uncrumple when valve 20 is compressed and uncompressed, respectively. Alternatively or additionally, the seats may comprise an elastic material, such as rubber silicone, that is configured to compress and stretch when valve 20 is compressed and uncompressed, respectively.

Reference is made to FIGS. 4A-C, which are schematic illustrations of a prosthetic valve 80, comprising a tubular element 82 and a valve member 84, in accordance with some applications of the invention. FIG. 4A shows valve 80 in a compressed configuration thereof, and FIGS. 4B-C show valve 80 in an expanded configuration thereof, and functioning, in accordance with some applications of the invention.

Typically, tubular element 82 comprises and/or has features of tubular element 22, described hereinabove (e.g., with reference to FIGS. 1A-D). For example, tubular element 82 defines a lumen 83 therethrough, typically comprises a frame that defines a plurality of cells, and is typically expandable (e.g., automatically) from a generally cylindrical compressed configuration (FIG. 4A) to a generally cylindrical expanded configuration (FIG. 4B).

Typically, valve member 84 comprises and/or has features of valve member 24, described hereinabove (e.g., with reference to FIGS. 1A-D and/or 2A-B). For example, valve member 84 is typically disc-shaped, typically comprises a frame that defines a plurality of cells, and is typically expandable (e.g., automatically) from a generally cylindrical compressed configuration (FIG. 4A) to a generally disc-shaped expanded configuration (FIG. 4B).

Typically, the dimensions of valve 80 (e.g., the dimensions of tubular element 82 and valve member 84) are similar (e.g., the same as) those of valve 20 (e.g., of tubular element 22 and valve member 24), described hereinabove, mutatis mutandis.

As shown in FIG. 4A, in the compressed configuration of valve 80, valve member 84, in the generally cylindrical compressed configuration thereof, is typically disposed within lumen 83 of tubular element 82, in the generally cylindrical compressed configuration thereof. As shown in FIG. 4B, in the expanded configuration of valve 80, valve member 84, in the generally disc-shaped expanded configuration thereof, is disposed within lumen 83 of tubular element 82, in the generally cylindrical expanded configuration thereof.

Valve 80 comprises covering 40, which covers at least part of the frames of tubular element 82 and valve member 84 (e.g., as described hereinabove for valve 20, mutatis mutandis). Typically, covering 40 covers an inner surface 96 of tubular element 82, and at least one side of valve member 84. Valve 80 is configured to be delivered percutaneously (e.g., transcatheterally and/or transluminally, such as transfemorally), e.g., as described hereinabove with respect to valve 20, mutatis mutandis.

Valve member 84 is coupled to tubular element 82 at one or more (e.g., two) coupling points 100, in both the compressed and expanded configurations of valve 80. Coupling points 100 comprise a coupling element, which may comprise a hinge, a connector (e.g., a connecting wire or suture), or any other suitable coupling element. For some applications, and as described for coupling element 61 hereinabove, each coupling element of valve 80 comprises a protrusion of the frame of the valve member protruding into a slot defined by frame of the tubular element.

Valve member 84 is coupled to tubular element 82 at the one or more coupling points 100, such that the valve member can move between (1) an open state in which the valve member generally allows fluid (e.g., blood) to flow through lumen 83, and (2) a closed state in which the valve member generally blocks lumen 83, thereby generally inhibiting fluid from flowing though the lumen. FIG. 4B shows valve member 84 (and thereby valve 80) in the closed state thereof, and FIG. 4C shows valve member 84 (and thereby valve 80) in the open state thereof.

Typically, valve member 84 is coupled to tubular element 82 at two coupling points 100 (e.g., coupling points 100a and 100b), such that valve member 84 can deflect (e.g., bend) around an axis a3 between the two coupling points. Typically, coupling points 100a and 100b lie on a central transverse axis a4 (e.g., a diameter) of tubular element 82, and axis a3 acts as a central fixed axis around which each resulting half of valve member 84 deflects. Further typically, and as shown in FIGS. 4A-C, the coupling element of valve 80 comprises a coupling rod 92, which is coupled to valve member 84 along axis a3, and to coupling points 100a and 100b, such that the valve member can move between the open and closed states by bending around the coupling rod. Coupling rod 92 is configured to be bent when valve 80 is compressed into the compressed configuration thereof (FIG. 4A), and to assume a generally straight configuration when the valve assumes the expanded configuration thereof (FIGS. 4A-B).

For some applications of the invention, valve member 84 comprises valve member 24, described hereinabove. For some applications of the invention, valve member 84 is unevenly rigid. For example, the valve member may define an area of increased flexibility at and/or around axis a3 (e.g., at and/or around coupling rod 92), so as to facilitate the movement of valve member 84 between the open and closed states described hereinabove. It is to be noted that, whereas valve member 24 of prosthetic valve 20 typically moves between the open and closed states thereof without changing shape, valve member 84 of prosthetic valve 80 typically does change shape when moving between the open and closed states thereof.

Valve 80 is configured such that valve member 84 moves between the open state and the closed state in response to changes in relative fluid pressure between each end of lumen 83, and thereby valve 80 is configured to act as a one way valve (e.g., a check valve). In the open state, a first end 104 of tubular element 82 is in fluid communication with a second end 106 of the tubular element. In the closed state, fluid communication between the two ends is reduced, compared to in the open state (e.g., the first and second ends are substantially not in fluid communication).

As shown in FIG. 4B, when fluid pressure at a second end 106 of tubular member 82 is higher than fluid pressure at a first end 104 of the tubular member (e.g., when fluid "tries" to move from the second end to the first end), valve member 84 is in (e.g., moves into) the closed state, thereby inhibiting flow of the fluid from the second end to the first end. As shown in FIG. 4C, when fluid pressure at first end 104 is higher than fluid pressure at second end 106 (e.g., when fluid "tries" to move from the first end to the second end), valve member 84 moves into the open state, thereby facilitating flow of the fluid from the first end to the second end. Thereby, valve 80 acts as a check-valve, first end 104 is an upstream end of the valve, and second end 106 is a downstream end of the valve.

For some applications of the invention, movement of valve member 84 between the open and closed states thereof is driven primarily by the relative pressure at each end of lumen 83. For some applications, valve member 84 is biased (e.g., shape-set) toward assuming the closed state, e.g., in the absence of any substantial forces thereon.

Valve member 84 is typically configured (e.g., dimensioned) such that, in the closed state, an outer edge 90 of the valve member is disposed close to inner surface 96 of tubular element 82 (e.g., the valve member is in close contact with the inner surface of the tubular element). For example, the diameter of valve member 84 is typically no more than 20% smaller than the width of the lumen of the tubular element.

For some applications of the invention, valve 80 further comprises a valve seat 102, configured to facilitate contact (e.g., sealing) between valve member 84 and tubular element 82. For some such applications, and as shown in FIGS. 4B-C, seat 102 is annular, and is disposed on the inner surface of tubular element 82, slightly closer than coupling points 100 to first end 104 of the tubular element. Seat 102 protrudes into lumen 83 of tubular element 82, so as to facilitate sealing between the tubular element and valve member 84. For some applications, the seats comprise a sealing element, such as a sealing surface, to further facilitate such sealing.

Typically, the seat and/or sealing element comprises a fabric, a resin and/or a polymer and is configured to fold, crumple, contract, and/or compress when valve 80 is compressed into the compressed configuration thereof (FIG. 4A), and to unfold, uncrumple, expand, and/or uncompress into the configuration shown in FIGS. 4B-C, when valve 80 is moved into the uncompressed configuration. For example, the seat may comprise a fabric, sutured to the frame of tubular element 82, and configured to crumple and uncrumple when valve 80 is compressed and uncompressed, respectively. Alternatively or additionally, the seat may comprise an elastic material, such as rubber silicone, that is configured to compress and stretch when valve 80 is compressed and uncompressed, respectively.

Reference is made to FIGS. 5A-C, which are schematic illustrations of a prosthetic valve 120, comprising a tubular element 122 and a valve member 124, in accordance with some applications of the invention. FIG. 5A shows valve 120 in a compressed configuration thereof, and FIGS. 5B-C show valve 120 in an expanded configuration thereof, and functioning, in accordance with some applications of the invention.

Typically, tubular element 122 comprises and/or has features of tubular element 22 and/or tubular element 82, described hereinabove (e.g., with reference to FIGS. 1A-D, and/or 4A-C). For example, tubular element 122 defines a lumen 123 therethrough, typically comprises a frame that defines a plurality of cells, and is typically expandable (e.g., automatically) from a generally cylindrical compressed configuration (FIG. 5A) to a generally cylindrical expanded configuration (FIG. 5B).

Typically, valve member 124 comprises and/or has features of valve member 24 and/or valve member 84, described hereinabove (e.g., with reference to FIGS. 1A-D, 2A-B and/or 4A-C). For example, valve member 124 is typically disc-shaped, typically comprises a frame that defines a plurality of cells, and is typically expandable (e.g., automatically) from a generally cylindrical compressed configuration (FIG. 5A) to a generally disc-shaped expanded configuration (FIG. 5B).

Typically, the dimensions of valve 120 (e.g., the dimensions of tubular element 122 and valve member 124) are similar (e.g., the same as) those of valve 20 (e.g., of tubular element 22 and valve member 24), described hereinabove, mutatis mutandis.

As shown in FIG. 5A, in the compressed configuration of valve 120, valve member 124, in the generally cylindrical compressed configuration thereof, is typically disposed within lumen 123 of tubular element 122, in the generally cylindrical compressed configuration thereof. As shown in FIG. 5B, in the expanded configuration of valve 120, valve member 124, in the generally disc-shaped expanded configuration thereof, is disposed within lumen 123 of tubular element 122, in the generally cylindrical expanded configuration thereof.

Valve 120 comprises covering 40, which covers at least part of the frames of tubular element 122 and valve member 124 (e.g., as described hereinabove for valves 20 and 80, mutatis mutandis). Typically, covering 40 covers an inner surface 136 of tubular element 82, and at least one side of valve member 84. Valve 80 is configured to be delivered percutaneously (e.g., transcatheterally and/or transluminally, such as transfemorally), e.g., as described hereinabove with respect to valves 20 and 80, mutatis mutandis.

Valve member 124 is coupled to tubular element 122 at at least one coupling point 140, in both the compressed and expanded configurations of valve 120. Valve 120 comprises a coupling element 141, which may comprise a hinge, a connector (e.g., a connecting wire or suture), or any other suitable coupling element. Typically, and as shown in FIGS. 5A-C, coupling element 141 comprises one or more struts 150 that protrude radially-inwardly from tubular element 122, and are coupled to a generally central point on valve member 124 (e.g., generally midway across the diameter of the valve member). Further typically, coupling element 141 comprises another strut 152 that is coupled to struts 150, extends longitudinally from struts 150, and couples struts 150 to valve member 124 by being coupled to the valve member.

Valve member 124 is coupled to tubular element 122 such that the valve member can move between (1) an open state in which the valve member generally allows fluid (e.g., blood) to flow through lumen 123, and (2) a closed state in which the valve member generally blocks lumen 123, thereby generally inhibiting fluid from flowing though the lumen. FIG. 5B shows valve member 124 (and thereby valve 120) in the closed state thereof, and FIG. 5C shows valve member 124 (and thereby valve 120) in the open state thereof. Typically, valve member 124 is coupled to tubular element 122 at coupling point 140 such that valve member 124 can deflect (e.g., bend, fold, and/or collapse) from the coupling point, such as by opening and closing in an umbrella-like or jellyfish-like fashion. Typically, coupling point 140 lies on a central longitudinal axis $a5$ of tubular element 122 and at the center of valve member 124. It is to be noted that, whereas valve member 24 of prosthetic valve 20 typically moves between the open and closed states thereof without changing shape, valve member 124 of prosthetic valve 120 typically does change shape when moving between the open and closed states thereof.

For some applications of the invention, valve member 124 comprises valve member 24 and/or valve member 84, described hereinabove. For some applications of the invention, valve member 124 is unevenly rigid. For example, the valve member may define one or more areas of increased flexibility that extend radially from coupling point 140 so as to facilitate the movement of valve member 124 between the open and closed states described hereinabove.

Valve 120 is configured such that valve member 124 moves between the open state and the closed state in response to changes in relative fluid pressure between each end of lumen 123, and thereby valve 120 is configured to act as a one way valve (e.g., a check valve). In the open state, a first end 144 of tubular element 122 is in fluid communication with a second end 146 of the tubular element. In the closed state, fluid communication between the two ends is reduced, compared to in the open state (e.g., the first and second ends are substantially not in fluid communication).

As shown in FIG. 5B, when fluid pressure at a second end 146 of tubular member 122 is higher than fluid pressure at a first end 144 of the tubular member (e.g., when fluid "tries" to move from the second end to the first end), valve member 124 is in (e.g., moves into) the closed state, thereby inhibiting flow of the fluid from the second end to the first end. As shown in FIG. 5C, when fluid pressure at first end 144 is higher than fluid pressure at second end 146 (e.g., when fluid "tries" to move from the first end to the second end), valve member 124 moves into the open state, thereby facilitating flow of the fluid from the first end to the second end.

Thereby, valve 120 acts as a check-valve, first end 144 is an upstream end of the valve, and second end 146 is a downstream end of the valve.

For some applications of the invention, movement of valve member 124 between the open and closed states thereof is driven primarily by the relative pressure at each end of lumen 123. For some applications, valve member 124 is biased (e.g., shape-set) toward assuming the closed state, e.g., in the absence of any substantial forces thereon.

Valve member 124 is typically configured (e.g., dimensioned) such that, in the closed state, an outer edge 130 of the valve member is disposed close to inner surface 136 of tubular element 122 (e.g., the valve member is in close contact with the inner surface of the tubular element). For example, the diameter of valve member 124 is typically no more than 20% smaller than the width of the lumen of the tubular element.

For some applications of the invention, valve 120 further comprises a valve seat 142, configured to facilitate contact (e.g., sealing) between valve member 124 and tubular element 122. For some such applications, and as shown in FIGS. 5B-C, seat 142 is annular, and is disposed on the inner surface of tubular element 122. Seat 142 protrudes into lumen 123 of tubular element 122, so as to facilitate sealing between the tubular element and valve member 124. For some applications, the seats comprise a sealing element, such as a sealing surface, to further facilitate such sealing.

Typically, the seat and/or sealing element comprises a fabric, a resin and/or a polymer and is configured to fold, crumple, contract, and/or compress when valve 120 is compressed into the compressed configuration thereof (FIG. 5A), and to unfold, uncrumple, expand, and/or uncompress into the configuration shown in FIGS. 5B-C, when valve 120 is moved into the uncompressed configuration. For example, the seat may comprise a fabric, sutured to the frame of tubular element 122, and configured to crumple and uncrumple when valve 120 is compressed and uncompressed, respectively. Alternatively or additionally, the seat may comprise an elastic material, such as rubber silicone, that is configured to compress and stretch when valve 120 is compressed and uncompressed, respectively.

Reference is again made to FIGS. 1A-5C. The prosthetic valves described hereinabove are typically configured to be compressed (e.g., crimped) so as to have a greatest diameter of less than 12 mm (e.g., less than 9 mm, such as less than 6 mm). The prosthetic valves described hereinabove are thereby typically advantageously configured to be delivered via a catheter that is 34 Fr or narrower (e.g., 24 Fr or narrower, such as 18 Fr or narrower), thereby facilitating percutaneous (e.g., transluminal, such as transfemoral) delivery.

Reference is again made to FIGS. 1A-5C. As described hereinabove, the valve member of each prosthetic valve is typically disposed within the lumen of the tubular element of that prosthetic valve, in both the compressed and uncompressed configurations of the prosthetic valve. It is to be noted that, for some applications, in the compressed configuration of the prosthetic valve, the valve member is disposed outside of the lumen of the tubular element. For example, in the compressed configuration of the prosthetic valve, the tubular element and the valve member may be generally collinear.

Reference is again made to FIGS. 1A-5C. As described hereinabove, the valve member of each prosthetic valve is typically coupled to the tubular element of that prosthetic valve, in both the compressed and uncompressed configurations of the prosthetic valve (e.g., during delivery and after implantation). It is to be noted that, for some applications, the valve member is intracorporeally couplable to the tubular element, such as after implantation of the tubular element. For example, the tubular element and valve member may be delivered sequentially, whilst connected via one or more guiding filaments, the guiding filaments facilitating juxtaposition and coupling of tubular element and valve member, such as by facilitating assembly of coupling element (e.g., by guiding a protrusion or rod into a slot).

Typically, the prosthetic valves described herein are implanted (and/or configured to be implanted) at a native valve of the subject such that the first end is upstream of the second end. For example, the valves may be implanted at an atrioventricular valve of the subject (e.g., a mitral valve of the subject) such that the first end is disposed in an atrium of the subject (e.g., a left atrium of the subject) and the second end is disposed in a ventricle of the subject (e.g., a left ventricle of the subject). Thereby, the prosthetic valve replaces one-way valve functionality of the native valve, with one-way valve functionality of the prosthetic valve.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for regulating blood flow of a subject, the apparatus comprising:
   a transluminally-implantable tilting-disc valve, the tilting-disc valve comprising:
      a frame:
         defining an arrangement of cells that shape the frame as a tubular element having a first end and a second end;
         having a compressed state in which the frame is generally cylindrical, has a compressed width, and is transluminally deliverable into the subject, and
         having an expanded state in which the frame is generally cylindrical, has an expanded width that is greater than the compressed width, and defines a lumen between the first end and the second end; and
      a valve member:
         coupled to the frame,
         disposed within the lumen in both the compressed and expanded states of the first frame,
         having a compressed state, and
         having an expanded state in which the valve member:
            is disc-shaped, and
            provides directional fluid flow through the lumen by tilting in response to changes in relative fluid pressure between the first end and the second end, such that at least part of the valve member moves toward the first end and at least part of the valve member moves toward the second end.

2. The apparatus according to claim 1, wherein the valve member provides directional fluid flow through the lumen without changing shape in response to changes in relative fluid pressure between the first end and the second end.

3. The apparatus according to claim 1, wherein the prosthetic valve further comprises a valve seat that protrudes into the lumen and facilitates sealing between the tubular element and the valve member.

4. The apparatus according to claim 3, wherein the valve seat is annular.

5. The apparatus according to claim 3, wherein the valve seat is a first arc-shaped valve seat, and wherein the prosthetic valve further comprises a second arc-shaped valve seat.

6. The apparatus according to claim 1, wherein the valve member is coupled to the first frame at two coupling points.

7. The apparatus according to claim 6, wherein the coupling points lie on a central transverse axis of the tubular element.

8. The apparatus according to claim 6, wherein the coupling points lie on a non-central transverse axis of the tubular element.

9. The apparatus according to claim 6, wherein the valve member provides directional fluid flow by the valve member rotating around an axis between the two coupling points in response to changes in relative fluid pressure between the first end and the second end.

10. The apparatus according to claim 6, wherein each of the coupling points comprises a hinge.

11. The apparatus according to claim 10, wherein each hinge is formed by a protrusion defined by the valve member protruding into a slot defined by the frame.

12. The apparatus according to claim 1, wherein the valve member is unevenly rigid.

13. The apparatus according to claim 1, wherein:
the frame is a first frame,
the valve member comprises a second frame and a covering,
in the expanded state of the valve member, the second frame has an inner edge that defines an opening, and the covering covers the second frame and the opening.

* * * * *